(12) United States Patent
Olek (10) Patent No.: US 9,926,599 B2
(45) Date of Patent: Mar. 27, 2018

(54) EPIGENETIC MARKER FOR THE IDENTIFICATION OF CD3CD4 POSITIVE T LYMPHOCYTES

(71) Applicant: Epiontis GmbH, Berlin (DE)

(72) Inventor: Sven Olek, Berlin (DE)

(73) Assignee: EPIONTIS GMBH, Berlin (DE)

( * ) Notice: Subject to any disclaimer, the term of this patent is extended or adjusted under 35 U.S.C. 154(b) by 39 days.

(21) Appl. No.: 14/353,671

(22) PCT Filed: Feb. 14, 2013

(86) PCT No.: PCT/EP2013/053009
§ 371 (c)(1),
(2) Date: Apr. 23, 2014

(87) PCT Pub. No.: WO2013/135454
PCT Pub. Date: Sep. 19, 2013

(65) Prior Publication Data
US 2015/0004602 A1 Jan. 1, 2015

Related U.S. Application Data

(60) Provisional application No. 61/609,580, filed on Mar. 12, 2012.

(51) Int. Cl.
*C07H 21/04* (2006.01)
*C12Q 1/68* (2006.01)

(52) U.S. Cl.
CPC ..... *C12Q 1/6881* (2013.01); *C12Q 2600/154* (2013.01)

(58) Field of Classification Search
None
See application file for complete search history.

(56) References Cited

U.S. PATENT DOCUMENTS

2009/0305234 A1* 12/2009 Olek .................... C12Q 1/6809
435/6.11

FOREIGN PATENT DOCUMENTS

| EP | 1 826 278 A1 | 8/2007 |
|---|---|---|
| EP | 2 199 411 A1 | 6/2010 |
| WO | WO 2006/094836 A2 | 9/2006 |

OTHER PUBLICATIONS

GenBank Accession NG_027688 GI 306518675 Jan. 31, 2011.*
Ushijima (Nature Reviews. 2005. 5: 223-231).*
Ehrlich et al. (Oncogene 2002. 21: 5400-5413).*
Baron, Udo et al. "DNA Methylation Analysis as a Tool for Cell Typing," *Epigenetics*, 2006, 1(1):55-60.
Deaton, Aimée M. et al. "Cell Type-Specific DNA Methylation at Intragenic CpG Islands in the Immune System," *Genome Research*, 2011, 21(7): 1074-1086.
Hughes, T. et al. "DNA Methylome in Human CD4+T Cells Identifies Transcriptionally Repressive and Non-Repressive Methylation Peaks," *Genes and Immunity*, Oct. 2010, 11(7): 554-560.
Komori, Kiyomi H. et al. "Application of Microdroplet PCR for Large-Scale Targeted Bisulfate Sequencing," *Genome Research*, Oct. 2011, 21(10): 1738-1745.
Luo, Juan et al. "Down-Regulation of Promoter Methylation Level of CD4 Gene after MDV Infection in MD-Susceptible Chicken Line," *BioMed Central Proceedings*, 2011, 5(4): S7.
Tutt Landolfi, Michelle M. et al. "Specific Demethylation of the CD4 Gene During CD4 T Lymphocyte Differentiation," *Molecular Immunology*, 1997, 34(1): 53-61.
Zou, Yong-Rui et al. "Epigenetic Silencing of CD4 in T Cells Committed to the Cytotoxic Lineage" *Nature Genetics*, 2001, 29(3): 332-336.

* cited by examiner

*Primary Examiner* — Jeanine A Goldberg
(74) *Attorney, Agent, or Firm* — Saliwanchik, Lloyd & Eisenschenk (57) ABSTRACT

The present invention relates to a method, in particular an in vitro method, for identifying CD3CD4 positive T lymphocytes of a mammal, wherein the method comprises analyzing the bisulfite convertibility of at least one CpG position in the CD3$^+$CD4$^+$ T helper cell specific non-methylated bisulfite convertible region according to SEQ ID No. 1, wherein a bisulfite convertibility of at least one CpG position to at least 90%, preferably to at least 91% and more preferably to at least 92% and most preferred to at least 95% in the sample is indicative for a CD4$^+$ T-lymphocyte cell, in particular a CD3$^+$CD4$^+$ T-lymphocyte cell. The present invention further relates to analyzing the bisulfite convertibility of at least one CpG position in the genes FLJ00060, FLJ38379, PPP6C, CD226, ZBTB7B and TNFAIP8 that are capable of positively identifying CD4 expressing cells in whole blood and segregate between CD4 and CD8 positive CD3 positive cells. Furthermore, the present invention relates to a kit for performing the above methods as well as respective uses thereof.

11 Claims, 2 Drawing Sheets

Figure 1

SEQUENCE LISTING

<160> NUMBER OF SEQ ID NOS: 13

<210> SEQ ID NO 1
<211> LENGTH: 1964
<212> TYPE: DNA
<213> ORGANISM: Homo sapiens

<400> SEQUENCE: 1

| | | | | | | |
|---|---|---|---|---|---|---|
| agggagtgaa | gactggagac | tatcccaggc | tgggaaaggc | gtggaaggca | actagtcgtg | 60 |
| ggcagttgag | gggagaagac | tggaagaggg | gaaaagagga | gaaaaagagt | gaagaagggg | 120 |
| agggaaaaaa | ttagaaagaa | taaataaata | taaggtggga | ggaaacctat | aaaaaagaaa | 180 |
| tgatgaggaa | aaacataaaa | acaagaaaaa | gagcaaaaga | agtggaatct | agtctagaga | 240 |
| aaattcttgc | aaaaccaatt | ttccttaacg | ggacaatctc | caaaaattga | caccaaatat | 300 |
| catacttgca | gcatttcata | agtcgcatga | tctatgtaat | agtctctttt | aactaccttt | 360 |
| tgtgtttctg | tgtgtatttt | taaattttg  | tctgcttctt | tgctcttta  | agattttga  | 420 |
| acaatgtcta | aaggcacttc | tactctagtt | agctttaaaa | tgattcatga | aataggaaag | 480 |
| ctaaaattct | cagaaagtgt | tgaaactgag | cttttgcgta | tgaattgccc | taaaagttgc | 540 |
| agatacatat | ctttagataa | atatgtcatt | taagaaacgg | attcgaaaag | aattggtggt | 600 |
| aggggtctca | tgaggccggg | agagttacag | aaggatgtgc | agccctcct  | gggcctggca | 660 |
| gggtgtgagg | gagagtgagg | actcactgtc | cctcctgaag | ggaagccctg | tgccatctca | 720 |
| gcctttccgc | cctcagacct | ttccagcccc | tgagacctca | tggccttgaa | gccgtgctat | 780 |
| ccccagtgtc | ctctgctttc | ccctcatagg | cttcttctgg | gagagaggtt | tcctggggta | 840 |
| cgttctgatc | cctcaaaacg | gaaaggccct | gttctcaata | attcaaagat | ttcactctga | 900 |
| gtgggatagt | gcttcctgaa | tgccctgctc | ttgtggtgga | catttttatc | ggggcaaggc | 960 |
| taagagcagg | gcctgatggg | ggaagtcact | gctacttcac | attttgacca | ataattcctt | 1020 |
| gtgctgtatc | agatgctgta | ggctgataca | aaatggccgc | cgccctcaaa | gtcagatgaa | 1080 |
| agagcccctg | aggacagcgt | tagagacact | cgggagatga | tttccctctt | tcaatgtggg | 1140 |
| agcacttaca | taggagaggt | ctatatctag | ataaaaactc | ctcccaccac | tggtgctaga | 1200 |
| cagagcttgg | gggcagccct | aggctctgac | cctggccgta | atggcggggt | ggtgctgagg | 1260 |
| gcaattggct | agaccaattg | tcttgcacgt | tttattttt  | attattattt | ttgagacgga | 1320 |
| gtctcgctct | cttgcccagg | ctggagtgca | atgacgtgat | ctccactcac | tgcagcctcc | 1380 |
| acctcctggg | ttcaagcgat | tctcctgcct | cagcctcttg | agtagctggg | attacaggag | 1440 |
| cccaacacca | cgcccggcta | cttttttgtat | ttttagtaga | gaccaggttt | cactatgttg | 1500 |
| gacaggctgg | cctcaaactc | ctggcctcaa | atgatccgcc | cgccttggcc | tcccaaagtg | 1560 |
| ctggcattac | agacgtgagc | caccatactg | ggccagtctt | gcacatttta | gacactcaat | 1620 |
| aaatgtttgt | tgaatgaaat | acctgtgatg | ggccgggcgt | ggtggcccac | accagtaatc | 1680 |
| ccagcccttt | gagaggccga | ggcaggagga | tggcttgaac | ctgggagttt | gagaccagcc | 1740 |
| tgggcaacat | ggtgaaaccc | ccatctctac | aaacccaca  | aaagttagct | gggcatggta | 1800 |
| gtgtgtgcct | gtggttccag | ctacttggga | agctgaggtg | ggaggattgc | ttgagcctgg | 1860 |
| gagacggagg | ctgcagtgag | gcctgactgt | gccactgcac | tccagcctgg | gcgagagtga | 1920 |
| ggccctgtct | caaaataact | ttgatgaagg | tggggaatca | gaag | | 1964 |

<210> SEQ ID NO 2
<211> LENGTH: 412

<212> TYPE: DNA
<213> ORGANISM: Homo sapiens

<400> SEQUENCE: 2

```
ttcttgcaaa accaattttc cttaacggga caatctccaa aaattgacac caaatatcat      60
acttgcagca tttcataagt cgcatgatct atgtaatagt ctcttttaac tacctttgt     120
gtttctgtgt gtattttaa attttgtct gcttctttgc tcttttaaga tttttgaaca      180
atgtctaaag gcacttctac tctagttagc tttaaaatga ttcatgaaat aggaaagcta     240
aaattctcag aaagtgttga aactgagctt ttgcgtatga attgccctaa aagttgcaga     300
tacatatctt tagataaata tgtcatttaa gaaacggatt cgaaaagaat tggtggtagg     360
ggtctcatga ggccgggaga gttacagaag gatgtgcagc ccctcctggg cc             412
```

<210> SEQ ID NO 3
<211> LENGTH: 399
<212> TYPE: DNA
<213> ORGANISM: Homo sapiens

<400> SEQUENCE: 3

```
cccctcatag gcttcttctg ggagagaggt ttcctggggt acgttctgat ccctcaaaac      60
ggaaaggccc tgttctcaat aattcaaaga tttcactctg agtgggatag tgcttcctga     120
atgccctgct cttgtggtgg acatttttat cggggcaagg ctaagagcag gcctgatgg      180
gggaagtcac tgctacttca catttgacc aataattcct tgtgctgtat cagatgctgt     240
aggctgatac aaaatggccg ccgccctcaa agtcagatga agagcccct gaggacagcg     300
ttagagacac tcgggagatg atttccctct ttcaatgtgg gagcacttac ataggagagg     360
tctatatcta gataaaaact cctcccacca ctggtgcta                            399
```

<210> SEQ ID NO 4
<211> LENGTH: 457
<212> TYPE: DNA
<213> ORGANISM: Homo sapiens

<400> SEQUENCE: 4

```
gctatcccca gtgtcctctg ctttcccctc ataggcttct tctgggagag aggtttcctg      60
gggtacgttc tgatccctca aaacggaaag gccctgttct caataattca aagatttcac     120
tctgagtggg atagtgcttc ctgaatgccc tgctcttgtg gtggcatttt ttatcggggc     180
aaggctaaga gcagggcctg atggggaag tcactgctac ttcacatttt gaccaataat      240
tccttgtgct gtatcagatg ctgtaggctg atacaaaatg gccgccgccc tcaaagtcag     300
atgaaagagc ccctgaggac agcgttagag acactcggga gatgatttcc ctctttcaat     360
gtgggagcac ttcataagga gaggtctata tctagataaa aactcctccc accactggtg     420
ctagacagag cttggggggca gccctaggct ctgaccc                              457
```

<210> SEQ ID NO 5
<211> LENGTH: 420
<212> TYPE: DNA
<213> ORGANISM: Homo sapiens

<400> SEQUENCE: 5

```
gtgctagaca gagcttgggg gcagccctag gctctgaccc tggccgtaat ggcggggtgg      60
tgctgagggc aattggctag accaattgtc ttgcacgttt tatttttat tattatttt      120
gagacggagt ctcgctctct tgcccaggct ggagtgcaat gacgtgatct ccactcactg     180
```

```
cagcctccac ctcctgggtt caagcgattc tcctgcctca gcctcttgag tagctgggat         240
tacaggagcc caacaccacg cccggctact ttttgtattt ttagtagaga ccaggtttca         300
ctatgttgga caggctggcc tcaaactcct ggcctcaaat gatccgcccg ccttggcctc         360
ccaaagtgct ggcattacag acgtgagcca ccatactggg ccagtcttgc acattttaga         420
```

```
<210> SEQ ID NO 6
<211> LENGTH: 22
<212> TYPE: DNA
<213> ORGANISM: Homo sapiens

<400> SEQUENCE: 6
ttcttacaaa accaattttc ct                                                   22

<210> SEQ ID NO 7
<211> LENGTH: 22
<212> TYPE: DNA
<213> ORGANISM: Homo sapiens

<400> SEQUENCE: 7
ggtttaggag gggttgtata tt                                                   22

<210> SEQ ID NO 8
<211> LENGTH: 22
<212> TYPE: DNA
<213> ORGANISM: Homo sapiens

<400> SEQUENCE: 8
cccctcataa acttcttcta aa                                                   22

<210> SEQ ID NO 9
<211> LENGTH: 22
<212> TYPE: DNA
<213> ORGANISM: Homo sapiens

<400> SEQUENCE: 9
tagtattagt ggtgggagga gt                                                   22

<210> SEQ ID NO 10
<211> LENGTH: 23
<212> TYPE: DNA
<213> ORGANISM: Homo sapiens

<400> SEQUENCE: 10
actatcccca atatcctcta ctt                                                  23

<210> SEQ ID NO 11
<211> LENGTH: 21
<212> TYPE: DNA
<213> ORGANISM: Homo sapiens

<400> SEQUENCE: 11
gggttagagt ttagggttgt t                                                    21

<210> SEQ ID NO 12
<211> LENGTH: 22
<212> TYPE: DNA
<213> ORGANISM: Homo sapiens

<400> SEQUENCE: 12
gtgttagata gagtttgggg gt                                                   22
```

```
<210> SEQ ID NO 13
<211> LENGTH: 26
<212> TYPE: DNA
<213> ORGANISM: Homo sapiens

<400> SEQUENCE: 13
tctaaaatat acaaaactaa cccaat                                              26
```

EPIGENETIC MARKER FOR THE IDENTIFICATION OF CD3CD4 POSITIVE T LYMPHOCYTES

CROSS REFERENCE TO A RELATED APPLICATION

This application is a National Stage Application of International Application Number PCT/EP2013/053009, filed Feb. 14, 2013; which claims the benefit of U.S. Provisional Application No. 61/609,580, filed Mar. 12, 2012; which are incorporated herein by reference in their entirety.

The Sequence Listing for this application is labeled "SeqList-23April14.txt", which was created on Apr. 23, 2014, and is 7 KB. The entire content of the sequence listing is incorporated herein by reference in its entirety.

The present invention relates to a method, in particular an in vitro method, for identifying CD3CD4 positive T lymphocytes of a mammal, wherein said method comprises analyzing the bisulfite convertibility of at least one CpG position in the $CD3^+CD4^+$ T helper cell specific non-methylated bisulfite convertible region according to SEQ ID No. 1, wherein a bisulfite convertibility of at least one CpG position to at least 90%, preferably to at least 91% and more preferably to at least 92% and most preferred to at least 95% in said sample is indicative for a $CD4^+$ T-lymphocyte cell, in particular a $CD3^+$ $CD4^+$ T-lymphocyte cell. The present invention further relates to analyzing the bisulfite convertibility of at least one CpG position in the genes FLJ00060, FLJ38379,-PPP6C, CD226, ZBTB7B and TNFAIP8 that are capable of positively identifying CD4 expressing cells in whole blood and segregate between CD4 and CD8 positive CD3 positive cells. Furthermore, the present invention relates to a kit for performing the above methods as well as respective uses thereof.

Furthermore, the present invention relates to a kit for performing the above methods as well as respective uses thereof. It is one aim of this invention to provide a novel, more robust means to quantitatively detect and measure particular subsets of T-lymphocytes of the blood within any solid organs or tissue or any body fluid of a mammal. Employing this method, the inventors provide for novel, not previously known means of determining, quantitating and routinely measuring CD4 T lymphocytes.

BACKGROUND OF THE INVENTION

T-lymphocytes are a major component of the mammalian immune system. Both CD4 and CD8 T-cells are responsible for proper functioning of said immune system. Whereas CD8 T-cells mediate the cytotoxic immune defense, CD4 cells—the so called T helper cells—assist both the humoral and the cell mediated immune defense.

CD4 (cluster of differentiation 4) is a glycoprotein expressed on the surface of T helper cells, monocytes, macrophages, and dendritic cells. In humans, the CD4 protein is encoded by the CD4 gene.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics - heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

Thus, for the purpose of definition for the present application, epigenetic modifications in the DNA sequence is referred to by the terminology of (i) non-bisulfite convertible cytosine (including 5-methylcytosine (mC), 5-hydroxymethylcytosine, (hmC)) and (ii) bisulfite convertible cytosine (5-formylcytosine, (fC) and/or 5-carboxycytosine (cC)). As both kinds of methylation, mC and hmC are not bisulfite convertible it is not possible to distinguish between these two. Likewise, fC, cC as well as non-modified cytosine are bisulfite convertible and can also not be distinguished from each other as well. The term methylated DNA encompasses mC as well as hmC. The term non-methylated DNA encompasses fC, cC, and non-modified DNA.

It is furthermore expected that novel variants of DNA modifications will be discovered in the future. Each type of modification will be either bisulfite-convertible or not. However, since the present method reliably distinguishes between the two groups, these novel modifications will also be usable for the method according to the present invention.

The primary target of the above-mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islan6 (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5 hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5 hmC were found in CpG islands associated with transcriptional regulators and in long interspersed nuclear elements. It is suggested that these regions might undergo epigenetic reprogramming in embryonic stem cells.

EP 1 213 360 describes a method of identifying a cell, tissue or nucleus, comprising collecting information on the methylation pattern of DNA, isolated from the cell, tissue or nucleus and analyzing the resultant information.

WO 2004/050706 describes a sub-group of T-cells, and relates to characteristics of regulatory T-cells which define them as such. The application also describes the uses of such T-cells, compositions comprising them, and chemokines which recruit them in the modulation of an immune response.

Finally, EP 1 826 279 describes a method, in particular an in vitro method, for identifying FOXP3-positive regulatory T cells, preferably CD25⁺ CD4⁺ regulatory T cells of a mammal, comprising analyzing the methylation status of at least one CpG position in the gene FOXP3 or an orthologous or paralogous gene thereof, and the use of DNA-methylation analysis of the gene of the transcription factor FOXP3 for a detection and quality assurance and control of regulatory T cells.

As mentioned above, recently three new cytosine modifications were discovered. Therefore, it is expected that future scientific findings will correct and overrule epigenetic patterns of modification described in the past. These past patterns of cytosine modification encompass bisulfite convertible (non-methylated, non-modified) and non-convertible (methylated, modified) cytosine. Both termini need to be redefined and corrected, since according to the novel scientific findings (i) non-bisulfite convertible cytosine encompasses 5-methylcytosine (mC) and 5-hydroxymethylcytosine (hmC), and (ii) bisulfite convertible cytosine encompasses 5-formylcytosine (fC), 5-carboxycytosine (cC) as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=*a/b* a=Σ(C and/or mC and/or hmC and/or fC and/or cC)
b=Σ(C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in. future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses the use of these modifications.

While the measurement and determination of CD4 cells is generally easy and is usually achieved through analyzing the expression of said antigens on the cellular surface; clinically, it remains challenging to specifically detect, identify, discriminate; and quantify CD4⁺ T cells, since the expression is not only specific for CD4⁺ T cells. Thus, the detection of CD4⁺ T helper lymphocytes, while desirous, is problematic, particularly for routine applications.

In view of the above, it is an object of the present invention to provide an improved and in particular robust method based on cytosine bisulfite convertibility analysis as a superior tool in order to more conveniently and reliably detect, identify, discriminate, and quantify CD4⁺ T-lymphocytes.

The present invention solves the above object by providing a method for identifying CD4⁺ T helper lymphocytes in a mammal, in particular in a sample derived from a mammal, comprising analyzing the bisulfite convertibility of at least one CpG position in the CD3⁺CD4⁺ T helper cell specific non-methylated bisulfite convertible region according to SEQ ID No. 1, wherein a bisulfite convertibility of at least one CpG position to at least 90%, preferably to at least 91% and more preferably to at least 92% and most preferred to at least 95% in said sample is indicative for a CD4⁺ T-lymphocyte cell, in particular a CD3⁺ CD4⁺ T-lymphocyte cell.

The present invention is based on the surprising finding of the inventors that the identification of a region of the CD4 gene as a specific epigenetic marker can greatly facilitate the clinical routine application of the analysis of the above markers. In the context of the present invention, this genomic region (see SEQ ID No. 1) is designated CD3⁺ CD4⁺ T helper cell specific non-methylated bisulfite convertible region. Surprisingly, the discriminatory pattern of bisulfite convertible and non-convertible cytosine is exclusively limited to this genomic region (according to SEQ ID No. 1) as represented and shown by the amplicons No. 1255, and Nos. 1999 to 2001. Consequently, amplicons (AMPs) located directly outside of region, either at the 5'-end (AMPs No. 32, 33, 1980) and at the 3'-end (AMPs No. 1981, 1982) do not show the discriminatory cytosine modification pattern. Therefore, the inventors have identified a highly CD3⁺ CD4⁺ T-cell-specific cytosine-modulated region including AMPs No. 1255 and 1999 to 2001. In the context of the present invention "bisulfite convertibility" includes both an analysis of individual and/or several cytosine modifications in order to detect a cytosine base ("C") that was methylated (and/or otherwise modified as described herein) in the original genomic sequence, versus a thymidine base ("T") instead of a cytosine that was non-methylated (and/or otherwise modified as described herein) in the original sequence, and therefore, in a preferred embodiment, was bisulfite converted.

In contrast to FACS and mRNA measurements, the respective measurement(s) can be done independent of purification, storage and to quite some extend also to tissue quality.

In a preferred embodiment of the method according to the present invention, said at least one CpG position is present in an amplicon selected from the group of amplicon No. 1255 according. to SEQ ID No. 2, No. 1999 according to SEQ ID No. 3, No. 2000 according to SEQ ID No. 4, and No. 2001 according to SEQ ID No. 5.

In another preferred embodiment of the method according to the present invention, said at least at least one CpG position is selected from position 26, 81, 274, 335, 341, and 374 of amplicon No. 1255 according to SEQ ID No. 2, position 42, 60, 151, 259, 262, 299, and 312 of amplicon No. 1999 according to SEQ ID No. 3, position 66, 84, 175, 283, 286, 323, and 336 of amplicon No. 2000 according to SEQ ID No: 4, and position 45, 53, 96, 125, 133, 163, 205, 259, 263, 345, 349, and 382 of amplicon No. 2001 according to SEQ ID No. 5.

The inventive concept is based on specific bisulfite convertibility (and preferably demethylation or non-methylation) of the $CD3^+CD4^+$ T helper cell specific region in CD4 positive T-lymphocytes. Using a simple and precise quantitative PCR method, the inventors show that specific pattern of cytosine modification of the CD4 gene region represents a specific marker for CD4 T-lymphocyte counts in blood or tissues. In one preferred embodiment one very good region is designated by the nucleotide sequence according to SEQ ID No. 1, which displays a different and thus differentiating bisulfite convertibility, when cells expressing $CD4^+$ are compared with all-other cells.

The inventors could demonstrate that in $CD4^+$ cells the CpG motifs are almost completely convertible by bisulfite (i.e. to more than 70%, preferably 80%, preferably, more than 90% and most preferred more than 95%), whereas the same motifs are completely methylated in all $CD4^-$ cells. Thus, determination of the bisulfite convertibility of the CD4 locus could become a valuable tool to identify T helper cells, such as will be required/or at least of some value for measuring T helper cells in autoimmune diseases, transplant rejections, cancer, allergy, primary and secondary immunodeficiencies, such as, for example, HIV infections and AIDS, or a T helper cells related immune status in any envisionable diagnostic context. The assay allows measurement of T helper cells without purification or any staining procedures. It even reports in solid tumors or other solid tissues the number of cells bisulfite convertible in said region, thus showing the total amount of CD4 positive tumor infiltrating T-lymphocytes.

The inventors found a bisulfite convertibility at the human CD4 locus to be restricted to T helper cells when tested against all major peripheral blood cell types and a selection of non-blood cells. These data indicated that epigenetic modifications in the CD4 locus serve as valuable marker for the identification of cells with the phenotype of T-lymphocyte, regardless of the expression of CD4.

In another preferred aspect of the method according to the present invention the bisulfite convertibility of at least one of the genes for GNGT2, CRTAM, IL2RB, and ZBTB32, or FLJ00060, FLJ38379, PPP6C, CD226, ZBTB7B, and TNFAIP8. The pattern of bisulfite convertibility of these genes thus also allow the unambiguous identification of all CD4 positive T lymphocytes. Thus, in a preferred embodiment of the method according to the present invention, said at least one CpG position is present in the 5' region upstream from the transcription start, promoter region, intron, and/or exon/intron border within the gene(s) for CD3 and/or CD8, in particular CD8 beta, or in the genes for GNGT2, CRTAM, IL2RB, and ZBTB32, or FLJ00060, FLJ38379, PPP6C, CD226, ZBTB7B, and TNFAIP8.

Equivalently, FLJ00060, FLJ38379, PPP6C, CD226, ZBTB7B and TNFAIP8 are capable of positively identifying CD4 expressing cells in whole blood.

Another preferred aspect of the method according to the present invention then further comprises the step of comparing of the relative amount of CD4 T cells as detected with CD3 T cells, CD8 T cells, regulatory T cells, monocytes, granulocytes, B cells, GAPDH, Th1, Th2, Th9, Th17, Th22, Tfh, NKT, and NK, most preferred with CD3 T cells, CD8 T cells, Treg and T helper cells. Using this step, diagnostically and therapeutically useful ratios of markers and respective cells can be determined and established based on analysis of the bisulfite convertibility of at least one CpG position in a gene selected from cell-specific genes of CD3 T cells, CD8 T cells, regulatory T cells, monocytes, granulocytes, B cells, GAPDH, Th1, Th2, Th9, Th17, Th22, Tfh, NKT, and NK. Preferred are the ratios between CD4 and CD3, CD-4 and CD-8, CD-4 and regulatory T cell markers, CD-4/helper T-cell markers.

Another preferred aspect of the method according to the present invention is directed at the use of cytosine modification analysis of the genes CD3 or SLA2, CHRNA3, C16orf24, LCK, FASLG, CD7, SIT1, IL32, CXCR6, UBASH3A, GRAP2, ITGB7 and TXK or GNGT2, CRTAM, IL2RB and ZBTB32 or FLJ00060, FLJ38379, PPP6C, CD226, ZBTB7B and TNFAIP8 for the detection and quality assurance and control of T lymphocytes.

In a preferred embodiment of the method according to the present_ invention, said analysis of bisulfite convertibility comprises amplification with at least one primer of suitable primer pairs that can be suitably designed based on SEQ ID No. 1, preferably oligomers according to any of SEQ ID No. 6 through 13.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)). With the amplification, the amplicon of the CD4 gene or any paralog or ortholog as described herein is produced that is a particularly preferred "tool" for performing the method(s) according to the present invention. Consequently, an, oligomer according to any of SEQ ID No. 6 or 7 or an amplicon as amplified by a primer pair based on SEQ ID No. 1 as mentioned above constitute preferred embodiments of the present invention.

The person of skill will furthermore be able to select specific subsets of CpG positions in order to minimize the amount of sites to be analyzed, for example at least one of CpG position 1, 2, 3, 4, 5, and 6 of the $CD3^+CD4^+$ helper T helper cell specific non-methylated bisulfite convertible region (SEQ ID No. 1), or all sites as present on the $CD3^+CD4^+$ T helper cell specific bisulfite convertible region according to SEQ ID No 1. The positions are numerically counted from the 5'-end of an amplicon (e.g. No. 1255, 1999, 2000 or 2001) as generated and analyzed. Preferred are combinations of 4, 5, 6, or 7 positions, which are producing enough information in order to be informative in the context of the present invention, wherein said at least one CpG position is selected from position 26, 81, 274, 335, 341, and 374 of amplicon No. 1255 according to SEQ ID No. 2, position 42, 60, 151, 259, 262, 299, and 312 of amplicon No. 1999 according to SEQ ID No. 3, position 66, 84, 175, 283, 286, 323, and 336 of amplicon No. 2000 according to SEQ ID No. 4, and position 45, 53, 96, 125, 133, 163, 205, 259, 263, 345, 349, and 382 of amplicon No. 2001 according to SEQ ID No. 5.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In another preferred embodiment of the method according to the present invention, the identification comprises a distinction of said $CD4^+$ T-lymphocytes from all major peripheral blood cell types and/or non-blood cells, preferably, but not limited to, from $CD19^+$ lymphocytes, $CD3^+$ $CD8^+$ T-Cells, $CD15^+$ granulocytes, $CD14^+$ monocytes, $CD56^+$ Natural Killer Cells and $CD3^+CD56^+$ Natural Killer T-Cells, and further, for example, hepatocytes, myocytes, chrondrocytes, keratinocytes and many other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, rat, monkey or human. The samples can be suitably pooled, if required.

Another preferred aspect of the method according to the present invention then further comprises the Step of concluding on the immune status of said mammal based on said T-lymphocytes as identified. The $CD4^+$ T-cell population can be quantified and be used as a benchmark to relatively quantify further detailed subpopulations (as Th1, Th2, Th9, Th17, Th22, Treg, Tth), or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from a primary or secondary immunodeficiency, such as AIDS, from autoimmune diseases, transplant rejections, cancer, infection diseases, and/or allergy, such as, but not limited to, idiopathic CD4+ lymphocytopenia, HIV, gastritis, diabetes, colitis, and lupus erythematodes.

Another preferred aspect of the method according to the present invention is related to a method for monitoring the level of $CD4^+$ T-lymphocytes in a mammal, comprising a method as above, and comparing the amount of $CD3^+$, i.e., overall T-lymphocytes as identified to an sample taken earlier or in parallel from the same mammal, and/or to a control sample. In yet another preferred embodiment of the methods according to the present invention, the mammal suffers from or is likely to suffer from a primary or secondary immunodeficiency, from autoimmune diseases, transplant rejections, cancer, and/or allergy, such as, but not limited to, idiopathic CD4+ lymphocytopenia, HIV, gastritis, diabetes, colitis, and lupus erythematodes.

Another preferred aspect of the method according to the present invention then relates to a method as above, further comprising measuring and/or monitoring the amount of said the amount of $CD^+$ T-lymphocytes in response to chemical and/or biological substances that are provided to said mammal, i.e. in response to a treatment of said patient. Based on the results as provided by the method(s) of the invention, the attending physician will be able to conclude on the immune status of the patient, and adjust a treatment of the underlying disease accordingly.

Another preferred aspect of the method according to the present invention relates to an oligomer according to any of SEQ ID No. 6 or 7, an oligomer designed based on SEQ ID No. 1, the $CD3^+CD4^+$ T helper cell specific non-methylated bisulfite convertible region according to SEQ ID No. 1 or an amplicon selected from any of SEQ ID No. 2 to 5.

Yet another preferred aspect of the present invention then relates to a kit for identifying and/or monitoring $CD4^+$ T-lymphocytes, in particular $CD3^+$ $CD4^+$ T-lymphocytes in a mammal based on the analysis of the bisulfite convertibility of at least one. CpG position in the $CD3^+CD4^+$ T helper cell specific non-methylated bisulfite convertible region according to SEQ ID No. 1 and/or at least one amplicon selected from any of SEQ ID No. 2 to 5, comprising materials for performing a method according the present invention as described herein. Preferably, said kit comprises a) a bisulfite reagent, and b) materials for the bisulfite convertibility analysis of at least one CpG position selected from the position 26, 81, 274, 335, 341, and 374 of amplicon No. 1255 according to SEQ ID No. 2, position 42, 60, 151, 259, 262, 299, and 312 of amplicon No. 1999 according to SEQ ID No. 3, position 66, 84, 175, 283, 286, 323, and 336 of amplicon No. 2000 according to SEQ ID No. 4, and position 45, 53, 96, 125, 133, 163, 205, 259, 263, 345, 349, and 382 of amplicon No. 2001 according to SEQ ID No. 5. Further preferred, the positions consist of positions 1, 2, 3, 4, 5, 6, 7, 8, 9, and 10 in the $CD3^+CD4^+$ T helper cell specific non-methylated region and/or said amplicons. Most preferred are 5, or 6 or all positions in the $CD3^+CD4^+$ T helper cell specific non-methylated region and/or said amplicons.

Finally, the present invention also encompasses the use of an oligomer or amplicon or a kit according to the present invention for identifying and/or for monitoring $CD3^+$ $CD4^+$ T-lymphocytes in a mammal.

In summary, using the CD4 marker, the inventors very specifically identified, quantified and particularly differentiated both CD4 positive T lymphocytes as such and in their relation to other cell types in a sample, for example to overall T-lymphocytes using the epigenetic markers for CD3, or their association to the CD8 cytotoxic T cells using the marker CD8beta and/or CD8alpha. By such means for example CD8 positive T-lymphocytes could then be further distinguished from CD4 lymphocytes. Thus, when using a combination of the present marker(s) and the CD8beta marker, CD4 and CD8 cells can be specifically distinguished. This was not possible before the invention, since the protein expression of the marker CD4 cannot be used to reliable identify and quantify CD4 T lymphocytes, nor was it possible from a (fresh, embedded or frozen) whole blood or tissue sample without specific means of conservation to provide a routine technology for the quantification of these cell types.

The invention will now be further described based on the following example and with reference to the accompanying figures and the sequence listing, without being limited thereto. For the purposes of the present invention, all references as cited herein are incorporated by reference in their entireties. In the Figures and Sequences.

SEQ ID No. 1 shows the genomic sequence of the CD3$^+$CD4$^+$ T helper cell specific non-methylated bisulfite convertible region according to the present invention.

SEQ ID No. 2 shows the genomic sequence of the amplicon No. 1255.

SEQ ID No. 3 shows the genomic sequence of the amplicon No. 1999.

SEQ ID No. 4 shows the genomic sequence of the amplicon No. 2000.

SEQ ID No. 5 shows the genomic sequence of the amplicon No. 2001.

SEQ ID No. 6 through 13 show the sequences of oligonucleotides used in the amplification of amplicon 1255, 1999, 2000 and 2001, respectively.

EXAMPLES

Example 1

CD4-Analysis

The inventors have purified various blood subsets, including CD3$^+$/CD4$^+$, CD3$^+$/CD8$^+$ nave and memory T lymphocytes, CD56$^+$ natural killer cells, CD19$^+$ nave and memory B cells, CD14$^+$ monocytes and CD15$^+$ granulocytes. DNA from the purified cells was bisulfite-treated and analyzed at various CpG dinucleotide motifs. The inventors then compared the non-bisulfite convertibility (finding C as for Cytosine that was methylated in the original sequence versus T for cytosine that was non-methylated in the original sequence and therefore bisulfite converted).

The data showed various CpG positions in a region of CD4 that were non-methylated in all CD3CD4 T-cells while methylated in all other blood cell types. The differentially cytosine-modified gene region as found for CD4 is shown in SEQ ID No. 1.

Figure 1:
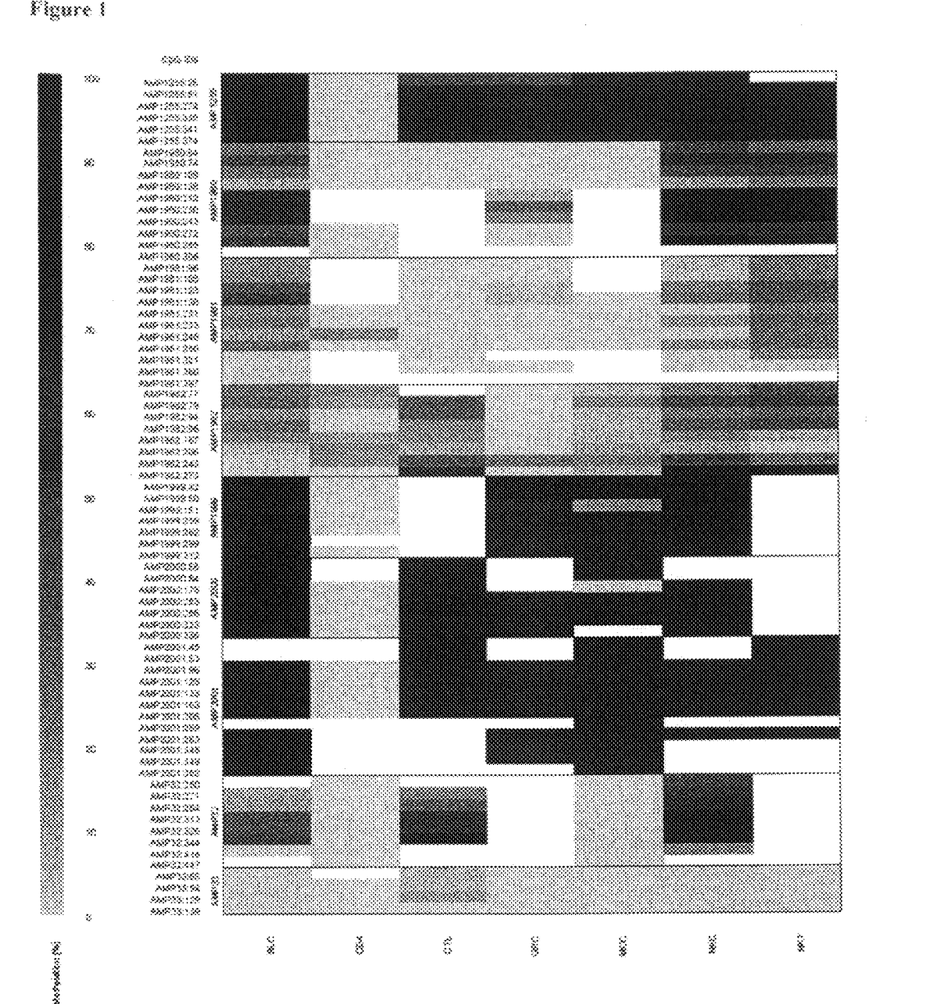
FIG. 1 shows the analysis of CpG sites on amplicons No. 1255 (SEQ ID No. 2), No. 1999(SEQ ID No. 3), No. 2000 (SEQ ID No. 4), and No. 2001 (SEQ ID No. 5) as well as control (negative) amplicons No. 32, 33, 1980, 1981, and 1981 of leukocyte populations (numbers on the left). The CpG positions of the respective amplicon as analyzed are as follows (from top to bottom, one box per CpG): AMP1255; 26, 81, 274, 335, 341, 374, AMP1980: 64, 74, 109, 136, 212, 230, 243, 272, 285, 306; AMP1981: 96, 105, 123, 136, 231, 233, 246, 250, 321, 360, 397; AMP1982: 77, 79, 94, 96, 167, 206, 243, 273; AMP1999: 42, 60, 151, 259, 262, 299, 312; AMP2000: 66, 84, 175, 283, 286, 323, 336; AMP2001: 45, 53, 96, 125, 133, 163, 205, 259, 263, 345, 349, 382; AMP32: 250, 271, 284, 313, 326, 344, 418, 447; and AMP33: 65, 94, 129, 139. The abbreviations on the bottom mean BLC15—CD19$^+$B lymphocytes, CD4—CD3$^+$CD4$^+$T helper cells, CTL—CD3$^+$CD8$^+$T-Cells, GRC—CD15$^+$granulocytes, MOC—CD14$^+$monocytes, NKC—CD56$^+$Natural Killer Cells; and NKT—CD3$^+$CD56$^+$Natural Killer T-Cells. Dark shading indicates high methylation, light shading low methylation.
Figure 2:
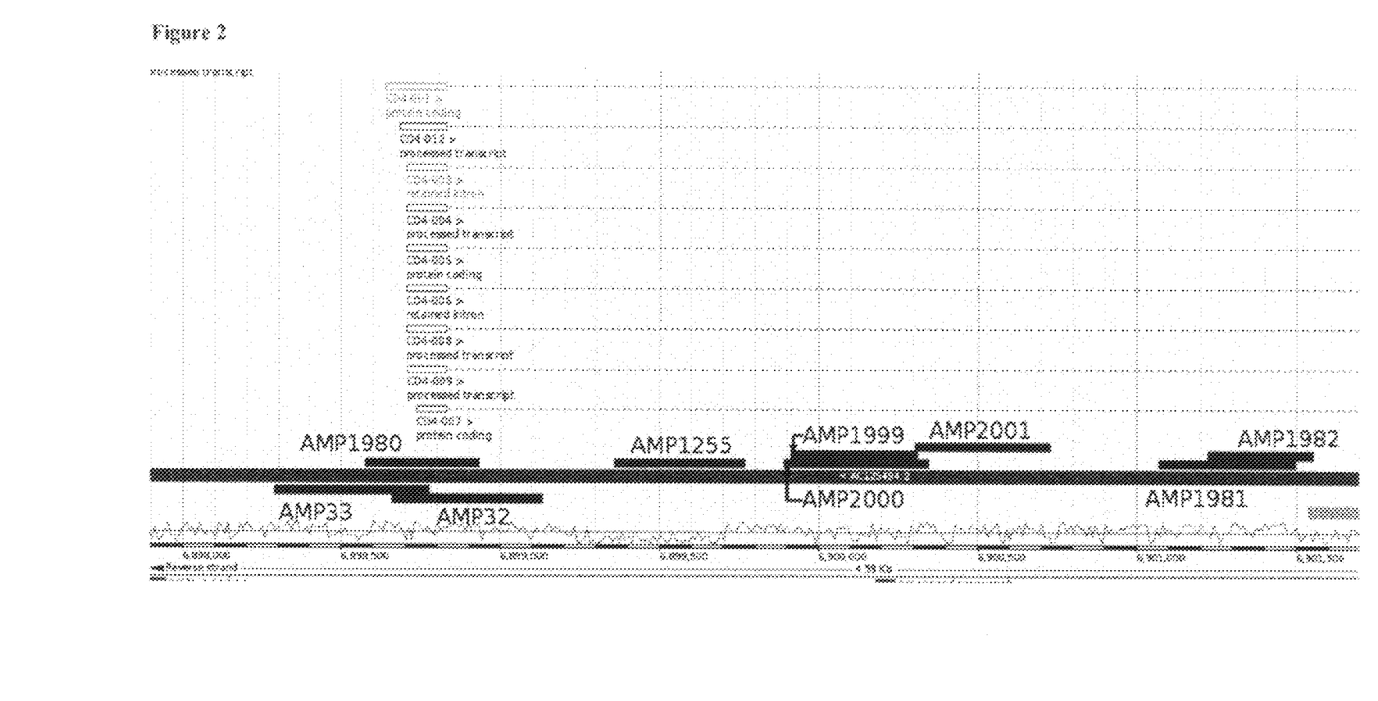
FIG. 2 shows the position of the CD3$^+$CD4$^+$ T helper cell specific non-methylated region according to the present invention and the alignment of amplicons as analyzed (bars at the bottom) against this region.

As examples for this region, several amplicons were found to show clear non-methylation (namely No. 1255, No. 1999, No. 2000 and No. 2001, see FIG. 1), whereas regions outside the CD3$^+$CD4$^+$ T helper cell specific non-methylated bisulfite convertibility region according to the present invention were methylated (as shown with amplicons No. 32, 33, and 1980-82, see also FIG. 1).

The data were unambiguous for the purified cell types. All CD4 T-lymphocytes were overwhelmingly non-methylated at all CG positions analyzed (see FIG. 1), whereas all other analyzed cell types were methylated at identical positions.

As an example, during the analyses, amplicon 1255, 1999, 2000, and 2001 were amplified with the following oligonucleotides (primers), respectively:

```
1255r:
                                            (SEQ ID No. 6)
5'-TTCTTACAAAACCAATTTTCCT-3'

1255q:
                                            (SEQ ID No. 7)
5'-GGTTTAGGAGGGGTTGTATATT-3'

1999r:
                                            (SEQ ID No. 8)
5'-CCCCTCATAAACTTCTTCTAAA-3'

1999q:
                                            (SEQ ID No. 9)
5'-TAGTATTAGTGGTGGGAGGAGT-3'

2000r:
                                            (SEQ ID No. 10)
5'-ACTATCCCCAATATCCTCTACTT-3'

2000q:
                                            (SEQ ID No. 11)
5'-GGGTTAGAGTTTAGGGTTGTT-3'

2001p:
                                            (SEQ ID No. 12)
5'-GTGTTAGATAGAGTTTGGGGGT-3'

2001o:
                                            (SEQ ID No. 13)
5'-TCTAAAATATACAAAACTAACCCAAT-3'
```

Example 2

Monitoring of CD4 Levels in Cancer Patients Undergoing Therapy.

The inventors quantified the amount of CD3+ and CD4+ T cells as well as level of CD4+ T cells as portion of CD3$^+$ T cell fraction by assessment of bisulfate convertibility of DNA in amplicon No. 2000 according to SEQ ID No. 4 (Table 1). Peripheral blood samples at two different time points during therapy follow up were used.

The results show patient specific changes of CD4+ T cell level and a reduced portion of CD4$^+$ cells in relation to CD3$^+$ T cell level during follow-up of cancer therapy which is related to drug efficacy, can indicate outcome prognosis, and/or can also predict therapy efficacy and safety.

TABLE 1

Assessment of CD4+ and CD3+ T cell levels of two patients (P1, P2) under a certain therapy. Two time points were assessed (1 and 2). Calculation of CD4+ and CD3+ cell levels following quantification of bisulfite convertible CpG containing regions via qPCR. (CP value) value to measure; (Standard Units) units corresponding to CP values calculated from standard curve; (% CD3, % CD4) relative amount of cells. (CD4/CD3 %) percentage of CD4 as portion of CD3.

| | CD4 Assay | | | | | | |
|---|---|---|---|---|---|---|---|
| Samples | PCR specific to TpG (bisulfite convertible, cell-type specific locus) | | | PCR specific to bisulfite convertible (cell-type independent locus) | | | |
| ID | CP Value | Standard units | vs | CP Value | Standard units | | % CD4 |
| P1-1 | 29.54 | 326.33 | | 26.76 | 3183.33 | | 10.25 |
| P1-2 | 28.54 | 633.33 | | 25.56 | 7310 | | 8.66 |
| P2-1 | 28.93 | 487.67 | | 25.59 | 7170 | | 6.8 |
| P2-2 | 26.71 | 2096.67 | | 23.78 | 24966.67 | | 8.4 |

| | CD3 Assay | | | | | | |
|---|---|---|---|---|---|---|---|
| Samples | PCR specific to TpG (bisulfite convertible, cell-type specific locus) | | | PCR specific to bisulfite convertible (cell-type independent locus) | | | |
| ID | CP Value | Standard units | vs | CP Value | Standard units | % CD3 | CD4/CD3 % |
| P1-1 | 29.97 | 540.67 | | 26.76 | 3183.33 | 16.98 | 60.4 |
| P1-2 | 27.75 | 2556.67 | | 25.56 | 7310 | 34.97 | 24.8 |
| P2-1 | 29.59 | 708 | | 25.59 | 7170 | 9.87 | 68.9 |
| P2-2 | 26.4 | 6600 | | 23.78 | 24966.67 | 26.44 | 31.8 |

The invention claimed is:

1. A method for identifying a cell as a CD4+ T helper cell in a sample derived from a human, the sample comprising one or more leukocytes selected from CD4+ T helper cell, CD19+ lymphocytes, CD3+CD8+ T-lymphocytes, CD15+ granulocytes, CD14+ monocytes, CD56+ natural killer cells, CD3+CD56+ natural killer cells, the method comprising the steps of:
   a) isolating genomic DNA from said sample,
   b) treating the isolated genomic DNA with bisulfite,
   c) amplifying a genomic region in the bisulfite treated genomic DNA with a primer pair of SEQ ID NOs: 12 and 13 to produce an amplicon, wherein the genomic region in the bisulfite treated genomic DNA corresponds to the genomic region consisting of SEQ ID NO: 5,
   d) performing a nucleic acid based assay on said amplicon to determine the methylation status of the CpG positions 125, 133, 163, and 205 in the genomic region consisting of the sequence of SEQ ID NO: 5, and
   e) identifying the cell as a CD4+ T helper cell when said CpG positions in the genomic region are methylated less than 10%.

2. The method according to claim 1, the method further comprising analysis of the methylation status of at least one CpG position in the genes for CD3 and/or CD8, or in the gene for GNGT2.

3. The method according to claim 1, wherein said sample is a blood sample; tissue, organ or cell sample; or a sample of blood lymphocytes.

4. The method according to claim 1, the method further comprising the step of evaluating the immune status of said human based on said CD4+ T helper cells as identified.

5. The method according to claim 1, the method further comprising the step of quantifying the relative amount of CD4+ T cells based on comparing the methylation status in the genomic region consisting of SEQ ID NO: 5 with the methylation status of a control gene.

6. The method according to claim 1, wherein said human has, or is likely to have, an autoimmune disease, transplant rejection, cancer, and/or allergy.

7. A method for monitoring the level of CD3+CD4+ T-lymphocytes in a human, the method comprising performing the method according to claim 1, and:
   a) determining the level of CD3+ overall T-lymphocytes in a sample taken earlier or in parallel from the human and/or to a control sample, and
   b) comparing the level of CD3+ overall T-lymphocytes as identified to the sample taken earlier or in parallel from the same human and/or to the control sample.

8. The method according to claim 6, the method further comprising measuring and/or monitoring the amount of said CD4+ T helper cells in response to a chemical and/or biological substance that is administered to said human.

9. The method of claim 1, wherein the cells in the sample consist of one or more cells selected from CD4+ T helper cell, CD19+ lymphocytes, CD3+CD8+ T-Cells, CD15+ granulocytes, CD14+ monocytes, CD56+ natural killer cells, and CD3+CD56+ natural killer T-cells.

10. A method for identifying the methylation status of at least one CpG position in a genomic region consisting of the sequence of SEQ ID NO: 5of human cell, the method comprising the steps of:
   a) isolating the genomic DNA from the human cell,
   b) treating said isolated genomic DNA with bisulfite, and
   c) amplifying a genomic region in the bisulfite treated genomic DNA with a primer pair of SEQ ID NOs: 12 and 13 to produce an amplicon, wherein the genomic region in the bisulfite treated genomic DNA corresponds to the genomic region consisting of SEQ ID NO: 5, and
   d) determining the methylation status of the at least one CpG position in the genomic region consisting of the sequence of SEQ ID NO: 5.

11. The method of claim 10, wherein the at least one CpG position is selected from positions 125, 133, 163, and 205 of SEQ ID NO: 5.

* * * * *

UNITED STATES PATENT AND TRADEMARK OFFICE
CERTIFICATE OF CORRECTION

PATENT NO. : 9,926,599 B2
APPLICATION NO. : 14/353671
DATED : March 27, 2018
INVENTOR(S) : Sven Olek Page 1 of 1

It is certified that error appears in the above-identified patent and that said Letters Patent is hereby corrected as shown below:

In the Specification

Column 2,
Line 38, "CpG islan6" should read -- CpG islands --.

Column 3,
Line 1, "DNA, isolated" should read -- DNA isolated --.

Column 4,
Lines 22-23, "discriminate;" should read -- discriminate, --.

Column 5,
Line 9, "position .is" should read -- position is --.
Line 35, "all-other" should read -- all other --.

Column 6,
Line 36, "present_invention" should read -- present invention --.
Lines 54-55, "an, oligomer" should read -- an oligomer --.

Column 8,
Line 32, "one. CpG" should read -- one CpG --.

Column 9,
Line 59, "nave and" should read -- naïve and --.
Line 60, "nave and" should read -- naïve and --.

Signed and Sealed this
Twenty-fifth Day of December, 2018

Andrei Iancu
*Director of the United States Patent and Trademark Office*